United States Patent [19]

Zupanovich

[11] Patent Number: 5,747,342

[45] Date of Patent: May 5, 1998

[54] METHODS AND APPARATUS FOR MONITORING AND CONTROLLING PH PHOSPHATE AND SODIUM TO PHOSPHATE RATIO IN BOILER SYSTEMS OPERATING WITH CAPTIVE ALKALINITY

[75] Inventor: John D. Zupanovich, Wexford, Pa.

[73] Assignee: Calgon Corporation, Pittsburgh, Pa.

[21] Appl. No.: 935,273

[22] Filed: Sep. 22, 1997

Related U.S. Application Data

[63] Continuation of Ser. No. 558,575, Oct. 31, 1995, abandoned.

[51] Int. Cl.$^6$ .................... G01N 31/16; G01N 31/22; G01N 33/18

[52] U.S. Cl. .................... 436/55; 210/739; 210/743; 422/62; 436/103; 436/163

[58] Field of Search .................... 436/55, 52, 103, 436/163; 422/62, 81; 210/739, 743, 143

[56] References Cited

U.S. PATENT DOCUMENTS

| | | | |
|---|---|---|---|
| 4,709,664 | 12/1987 | Barto et al. | 122/379 |
| 4,833,622 | 5/1989 | Barto et al. | 364/496 |
| 5,019,342 | 5/1991 | Muccitelli et al. | 422/16 |
| 5,240,681 | 8/1993 | O'Lear et al. | 422/82 |
| 5,252,486 | 10/1993 | O'Lear et al. | 436/52 |

OTHER PUBLICATIONS

Pederson, et al., *Anal. Chim. Acta*, 238, 191–199 (1990).

Steele, et al., *SPE–Enhanced Coordinated PO$_4$/pH Control Improves Boiler Operating Reliability*, Off. Proc. Int'l. Water Conf., 53rd, 409–414 (1992).

Makela, et al., *Interact. Iron–Based Mater. Water Steam*, Proc. Int. Conf., TR-102101, Nov. 1–Nov. 21 (1993).

Mooney, *Instrumentation In The Power Industry Proceedings*, 34, 425–50 (Jun., 1991).

Boyette, et al., *An Automated Coordinated Phosphate/pH Controller For Industrial Boilers*, NACE Conference, 624/1–10 (1995).

*Primary Examiner*—Jan Ludlow
*Attorney, Agent, or Firm*—Webb Ziesenheim Bruening Logsdon Orkin & Hanson, P.C.

[57] ABSTRACT

Methods and apparatus for monitoring and controlling pH, phosphate, and sodium to phosphate ratio in boiler systems operating with captive alkalinity chemistry are described. The methods for monitoring and controlling these parameters include the steps of determining the phosphate concentration via FIA, determining the pH, and using these values to determine the sodium to phosphate ratio. These values are then compared to the optimum values for the boiler system being treated; on the basis of this comparison, adjustments to the feed rate of water treatment chemicals being added to the system are then made. The apparatus includes a device for determining phosphate concentration via FIA, a device for determining pH, a means for determining sodium to phosphate ratio and a device for adjusting the feed rate of water treatment chemicals being added to the system. The device for adjusting the chemical feed rate is computer controlled.

8 Claims, 11 Drawing Sheets

METHODS AND APPARATUS FOR MONITORING AND CONTROLLING PH PHOSPHATE AND SODIUM TO PHOSPHATE RATIO IN BOILER SYSTEMS OPERATING WITH CAPTIVE ALKALINITY

This application is a continuation of application Ser. No. 08/558,575 filed on Oct. 31, 1995 now abandoned.

FIELD OF THE INVENTION

The present invention relates to methods and apparatuses generally useful for monitoring and/or controlling three related chemical parameters in a boiler system operating with captive alkalinity chemistry control—pH, phosphate and sodium to phosphate ratio. More particularly, this invention relates to methods and apparatuses useful for maintaining these three chemical parameters within predetermined, desired ranges through the addition of one or more water treatment chemicals containing sodium and/or phosphate.

BACKGROUND OF THE INVENTION

Treatment of water used for steam generation, such as in a boiler system, generally involves, among other things, maintaining various water chemistry parameters in accordance with often rigid specifications. Typically, these specifications set forth acceptable ranges into which the chemistry parameters being maintained should fall. Parameters maintained by system operators include, inter alia, pH, sodium concentration, phosphate concentration and the ratio of sodium to phosphate. In maintaining the system, the operator must first determine the level of each parameter and then determine how to adjust each parameter so as to maintain each parameter within its acceptable range. The present invention is directed to automated means for making these determinations.

The boiler system environment can be generally described as harsh, having an alkaline pH and operating at high temperatures and pressures (i.e. temperatures above about 100° C. and pressures above about 900 psig). This environment is intolerant to deviations from the chemistry specifications or contaminants in the system. Contaminants can affect various water chemistry parameters in the system, and can therefore greatly increase the difficulty of keeping these parameters within the specified acceptable range. For example, contaminants can cause fluctuation in the pH of the system. Contaminants can also cause carryover of chemicals from the boiler to the steam side of the system, and lead to deposits and corrosion throughout the system.

Deposits are formed when the concentration of a particular contaminate exceeds its solubility and therefore precipitates out of solution. Typically in the form of scale or sludge, deposits can form on any of the boiler equipment, although the boiler tubes are particularly susceptible. Scale on the boiler tubes reduces the heat transfer ability of the tubes which in turn reduces the efficiency of the boiler unit as a whole. Also, scale and other deposits can increase the potential for boiler tube failure. The problem becomes more severe in systems with high heat transfer rates and in high pressure boilers.

Corrosion is another problem which negatively impacts operation of a boiler, and is most typically exemplified by the attack of steel by oxygen. This attack can occur in any portion of the boiler system in which oxygen is present. High temperatures and low pH conditions generally accelerate oxygen attack. Corrosion can also result from alkali or acid attack, which is most typically seen in high pressure boilers when caustic concentrates in local areas. Failure to maintain water chemistry within specifications is also believed to contribute to a corrosive environment.

Corrosion, like deposits, generally decreases the efficiency of the boiler unit. Corroded boiler tubes which cannot conduct water must be taken out of service; each tube taken out of service reduces the available heat transfer surface in the unit. Often times, the problem of corroded boiler tubes may be severe enough to mandate replacement of the tubes, or even the boiler itself. Such replacements are costly and require shutdown of the system. In addition, the settling of corrosion products can lead to sludge accumulation in the boiler system, which may contribute to further problems with corrosion and heat transfer efficiency.

One way to combat potential problems such as deposits and/or corrosion in the boiler system is through internal treatment with corrective chemicals of the boiler feedwater, the boiler water itself, the steam or the condensate. One type of chemical internal treatment of boiler water is known in the art as coordinated phosphate/pH or captive alkalinity treatment. The present invention is directed to methods and apparatuses for use in boiler systems which employ this type of chemical treatment. Captive alkalinity is typically recommended for boiler systems which use demineralized quality make-up water and in which the internal treatment program must contribute little solids to the system, such as, for example, those boilers with high heat transfer rate.

It is desirable to have some alkalinity in the water for the system to achieve its optimum pH and to help prevent corrosion of the boiler internals. Alkalinity generally promotes formation of a protective iron oxide film on the boiler tubes which deters corrodants. If the alkalinity is too high, however, it can lead to corrosion. For example, high concentrations of caustic, such as sodium hydroxide (NaOH), can form a concentrating film on boiler tubes which results in caustic attack or caustic gouging usually characterized by pits or grooves in the boiler tube. This film attacks the protective oxide layer and provides a fresh site for steel oxidation and further caustic attack.

Captive alkalinity control is designed to prevent the formation of free caustic in the system; "free caustic" as used herein generally describes any unbonded, strongly alkaline material. Proper control of boiler water pH and phosphate through captive alkalinity control is believed to ensure the elimination, or at least the reduction, of free caustic. This is particularly important in a boiler system operating at high temperatures, since the potential for caustic attack increases with temperature. By reducing free caustic, the occurrence of boiler tube failure due to concentrating film attack may also be reduced.

In captive alkalinity control, the reduction of concentrating caustic films, as well as the maintenance of pH, phosphate concentration and sodium to phosphate ratio, is accomplished with a phosphate buffer—typically disodium phosphate and either monosodium phosphate or trisodium phosphate. All of these compounds contribute both sodium and phosphate to the system being treated. In addition, sodium hydroxide and phosphoric acid themselves can also be used to adjust the sodium to phosphate ratio, although they typically aren't preferred. Maintaining the sodium to phosphate molar ratio between 2:1 and 3:1 typically will keep the pH and phosphate concentration of the system within acceptable ranges. Captive alkalinity treatment generally operates under the theory that if the boiler water pH is maintained at or below that pH which exists when the sodium to phosphate ratio is about 3:1, then no free caustic will be present in the bulk boiler water. The ideal sodium to phosphate ratio ($Na:PO_4$) will vary from system to system, but in general the optimum ratio will be between about 2.2:1 and 2.8:1.

The pH and phosphate concentration are used to determine the sodium to phosphate ratio. Standardized captive alkalinity curves, which will be familiar to one having ordinary skill in the art, represent the sodium to phosphate ratios which correspond to various pH and phosphate measurements. These captive alkalinity curves are best described in terms of a graph, with pH on the X-axis and phosphate on the Y-axis. The optimum sodium to phosphate range will be depicted on this graph in terms of a "target box" which corresponds to an optimum pH range and an optimum phosphate range. The target box will be different for every system, depending primarily on the pressure at which the system operates. For example, a pH of 9.0 and a phosphate concentration of 7 parts per million (ppm) would typically be within the target box for a unit operating between approximately 1500 and 2000 psig of pressure, but would be outside the target box for units operating at less than 1500 psig or more than 2000 psig. Ideally, the apparatus of the present invention will be programmed to maintain the sodium to phosphate ratio in the center of the target box, as the center represents the optimum sodium to phosphate ratio.

In addition to the role they play in determining the sodium to phosphate ratio, the pH and phosphate concentrations are important for other reasons. Out of specification pH may lead to corrosion of boiler internals. Caustic attack, discussed above, is an example of a corrosion problem related to pH. Concentrating films can also be formed when acidic compounds containing such ions as chloride, sulfate, or phosphates are present in the boiler environment. Although specifications will vary from system to system, the boiler pH should generally be maintained in an alkaline range, preferably a range of about 8 to 11.

Monitoring and controlling phosphate concentration is also important in boiler systems. In addition to being used as a buffer to maintain pH in captive alkalinity treatment, phosphates are used in aqueous systems such as boilers to prevent calcium scales and steel corrosion. Another purpose for measuring phosphate concentration is to avoid high total phosphate concentrations which may result in the formation of insoluble phosphate salts. All of the phosphate which exists in a boiler system will be in the form of inorganic orthophosphate. This is because the temperatures and pressures of the boiler systems are so high that any other forms of phosphate which are introduced to the boiler system will be converted to inorganic orthophosphate.

Other parameters evaluated in determining the sodium to phosphate ratio may include, inter alia, the pressure at which the boiler operates, the temperature at which the boiler operates, the quality of water which is being used in the system, and the ability of the operator to exclude contaminants from the system. For example, a system operating at a higher pressure will require lower solids—that is lower phosphates—to maintain the sodium to phosphate ratio in the desired range; the same is true for systems using a higher purity water.

Currently, the calculation and maintenance of the sodium to phosphate ratio is done manually. Typically, this ratio is determined only once a day, with no subsequent determination of sodium to phosphate ratio made until the following day. The sodium phosphates or other chemicals added to maintain the system within an acceptable sodium to phosphate ratio are prepared and fed daily based on this one sodium to phosphate ratio product. This method does not allow for real time analysis, and results in wide fluctuations in control. Further, adjusting the sodium to phosphate ratio usually requires the supplemental feed of NaOH along with the phosphate product, or frequent manual pump adjustment. In short, manual control of the sodium to phosphate ratio requires considerable manpower with often imprecise results.

U.S. Pat. Nos. 5,252,486 and 5,240,681 disclose methods and apparatuses, respectively, for monitoring the inorganic phosphate content in aqueous systems using flow injection analysis (FIA) apparatus. Neither of these patents, however, disclose the simultaneous monitoring of pH or the automated control of any of these parameters.

Pederson et al, *Anal. Chim. Acta*, 238, 101–199 (1990) disclose a system wherein on/off switching control of a municipal pilotscale wastewater treatment aeration tank is based on a flow injection analysis of ammonium content.

Steele et al, *SPE-Enchanced Coordinated $PO_4$/pH Control Improves Boiler Operating. Reliability*, Off. Proc. Intl. Water Conf., 53rd, 409–14 (1992) discuss the use of a coordinated phosphate/pH control program along with a process control package to enhance operational control and readily detect upsets. The reference does not discuss, however, the use of automated and/or on-line analysis of either phosphate or pH; nor does the reference discuss the use of automated chemical feed to maintain system control, as is claimed in the present invention.

Makela et al, *Interact. Iron-Based Mater. Water Steam*, Proc. Int Conf., issue TR-102101, 11/1–11/21, (1993) discuss the importance of on-line pH measurements and a device for making this measurement, as well as the influence of phosphates on pH. The reference does not discuss on-line phosphate analysis, coordinated phosphate/pH control or an automated means for controlling chemical feed as is claimed in the present invention.

Mooney, E. F., *Instrumentation In The Power Industry Proceedings*, 34, 425–50 (June, 1991) discusses photometric measurement of copper, silica, phosphate and sulfate by using a fiber optics probe photometer. The reference does not discuss use of these measurements in the control of chemical feed, as is claimed in the present invention.

Boyette et al, *An Automated Coordinated Phosphate/pH Controller For Industrial Boilers*, NACE Conference, p 624/1–624/10 (1995) disclose a means for controlling phosphate and pH in boiler systems. The reference does not disclose the use of FIA to determine the phosphate content of the system, as is claimed in the present invention. In addition, the control mechanism disclosed by Boyette operates via an on/off pumping mechanism which pumps only one feed product at a time. In contrast, the present invention claims methods and apparatus which can proportionally feed two products simultaneously.

None of these references disclose methods or apparatus for the automated monitor and control of pH, phosphate and sodium to phosphate ratio. Accordingly, there is a need for methods and apparatus which allow for such monitor and control.

SUMMARY OF THE INVENTION

The present invention generally meets the above described need by providing methods and apparatus for monitoring and/or controlling pH, phosphate and the sodium to phosphate ratio of a boiler system operating on captive alkalinity chemistry control. The methods of the present invention comprise the steps of: a) determining the phosphate content of the boiler system by using, flow injection analysis (FIA); b) determining the pH of the boiler system; c) calculating the sodium to phosphate ratio; and d) controlling the feed rate of at least one water treatment chemical being added to said system so as to maintain the pH, phosphate concentration and sodium to phosphate ratio within desired ranges. The computer can be set to respond to a variety of different conditions. For example, it can be set to feed phosphate(s) if the phosphate content is the only parameter out of range, if the pH is the only parameter out of range, or if both phosphate out of range. Typically, if pH or phosphate are out of range, the sodium to phosphate ratio will also be out of range.

FIA is a simple and reliable technique based on continuous flow of a sample solution which is introduced directly into an unsegmented carrier stream of a reagent solution, thereby forming a well-defined sample zone. While it is being transported to a detector device further downstream, the sample has an opportunity to react with the reagent and form a new chemical species which can be quantitatively measured by the detector. The reaction is usually a color-forming one and the detector a colorimeter (spectrophotometer), an electrode, or the like. FIA lends itself to the automated, rapid and reliable analysis of various samples, and offers many advantages over the older technique of air-segmented continuous flow analysis.

The present invention also provides an apparatus for monitoring and/or controlling of pH, phosphate, and sodium to phosphate ratio. The apparatus comprises an in-line phosphate monitor, preferable an FIA apparatus such as that disclosed in U.S. Pat. No. 5,240,681, and an in-line pH meter. Both the phosphate monitor and pH meter are attached to a controller, preferable a computer. The computer receives output signals which represent the pH and phosphate content. If an FIA apparatus is used, it will typically have its own computer, so a separate controller will not be needed; in this embodiment, the signal from the pH meter will be sent directly to the FIA apparatus.

In yet another embodiment, the FIA apparatus itself is equipped with a pH meter which is directly read by the FIA computer.

The controller, which is programed to calculate the sodium to phosphate ratio from the pH and phosphate values, also controls one or more means for feeding chemicals, preferably chemical feed pumps. These pumps, in turn, control the amount of phosphate being fed to the boiler system. Based on the signal received from the controller, the pumps will control the rate of chemical feed so that the amount of phosphate(s) necessary to maintain the parameters within the desired ranges are added to the system.

DETAILED DESCRIPTION OF THE INVENTION

Figure 1:
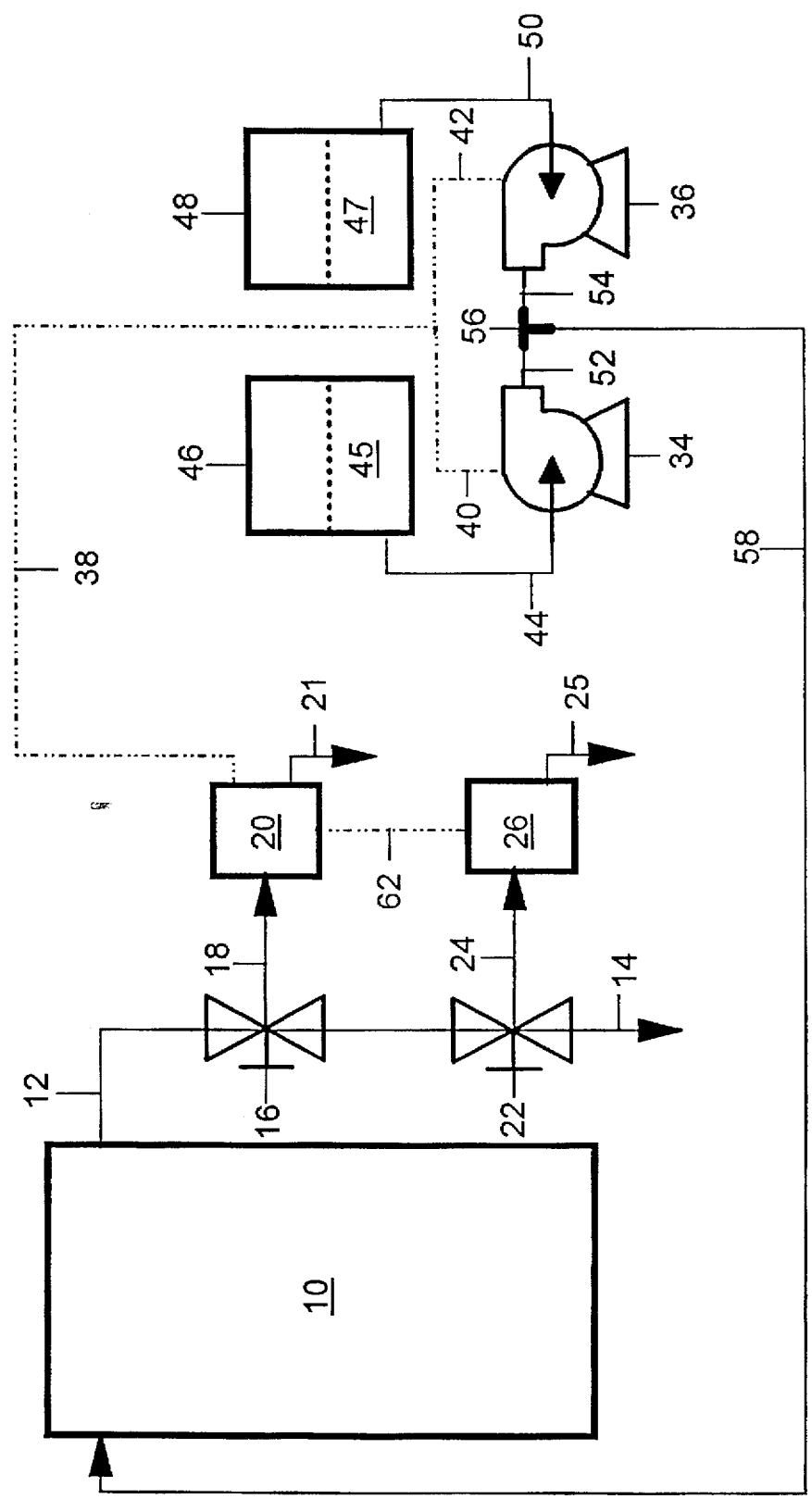
FIG. 1 is a schematic diagram of the apparatus according to the present invention.

The present invention is directed to methods and apparatuses for the automated monitoring and/or controlling of pH, phosphate, and sodium to phosphate ratio ($Na:PO_4$) in boiler systems operating with captive alkalinity chemistry control. Specifically, the present invention is directed to a method for monitoring and/or controlling pH, phosphate concentration and sodium to phosphate ratio in a boiler system using captive alkalinity, comprising the steps of: a) determining the phosphate concentration of said system by using flow injection analysis (FIA); b) determining the pH of said system; c) calculating the sodium to phosphate ratio; and d) controlling the feed rate of at least one water treatment chemical being added to said system so as to maintain the pH, phosphate concentration and sodium to phosphate ratio within desired ranges. The present invention is further directed to an apparatus for monitoring and/or controlling pH, phosphate concentration and sodium to phosphate ratio in a boiler system operating on captive alkalinity, comprising: a) an FIA means for determining the phosphate concentration of said system; b) a means for determining the pH of said system; c) a means for determining the sodium to phosphate ratio of said system; and d) a means for controlling, feed rate of at least one water treatment chemical being added to said system so as to maintain pH, phosphate concentration and sodium to phosphate ratio within desired ranges.

Generally, the pH, phosphate, and sodium to phosphate parameters can be controlled by varying, the rate of chemicals fed, i.e. the amount of water treatment chemical(s) added to the boiler system. In the most preferred embodiment of the present invention, a combination of disodium phosphate and trisodium phosphate should be used to maintain these parameters within their desired range. The automated control provided for in the methods of the present invention allows for the real time analysis of these critical boiler water parameters and prompt response to out of specification conditions. The user of the present invention will also minimize blowdown loss attributable to control problems. The methods and apparatus of the present invention further provide improved reliability, and safe and direct measurement and chemistry control, thereby offering several advantages over current methods and apparatus. In addition, the methods and apparatus of the present invention can be adapted to suit the needs of each individual user; this is important because control parameters generally vary from one boiler system to the next.

The methods of the present invention require a continuously flowing sample stream running from the boiler system. Two take-off valves are established in the sample stream to allow a portion of the sample stream to be drawn off for phosphate analysis and a separate portion to be drawn off for pH analysis. The first take-off valve is attached to a conduit which runs to an in-line phosphate monitor. The sample runs continuously; when not being monitored, or after monitoring, the sample stream runs to waste.

Step a) of the present invention requires that the phosphate monitor be a flow injection analysis (FIA) apparatus. An FIA apparatus suitable for use in the methods of the present invention is disclosed in U.S. Pat. No. 5,240,681. The method of using an FIA apparatus for determining total inorganic phosphate content is disclosed in U.S. Pat. No. 5,252,486.

To carry out step b), the second take-off valve from the sample stream is generally attached to a conduit which runs to an in-line pH meter. Any standard pH meter can be used, such as those available from Fischer Scientific, Inc. or the Orion Co. Again, the sample runs continuously; when not being monitored or after passing, through the pH meter the sample stream runs to waste. Since the pH meter is capable of monitoring pH on a continuous basis, continuous signal representing the pH of the sample will therefore be emitted.

Signals from both the FIA monitor and the pH meter are sent to a controller, preferably a computer which typically will be part of the FIA apparatus. This can be accomplished by any suitable wiring means known in the art. Step c) is then carried out by the computer, which utilizes the signals from the pH meter and phosphate monitor and, together with pre-programmed data, calculates the sodium to phosphate ratio. The computer is pre-programmed to compare pH and phosphate values it receives from the pH meter and phosphate monitor with captive alkalinity curves, which are also pre-programmed into the computer. From this comparison, the computer determines the sodium to phosphate ratio of the system. If the sodium to phosphate ratio is in the center of the target box, then no adjustments to the chemical feed rate will be made. If, however, the sodium to phosphate ratio is not in the center of the target box, or not in the target box at all, the computer will determine the amount of sodium phosphate, if any, needed to put the sodium to phosphate ratio back into the target box.

Relative to step d), controlling the feed rate of at least one water treatment chemical, the computer is programmed to make adjustments to the chemical feed rate based on: only the phosphate reading; only the pH reading; either the pH or the phosphate reading; or on both the phosphate and pH readings. For example, the computer can be programmed to change the feed rate if only the phosphate is out of its target range. In this scenario, the feed rate of phosphate will not be changed if the phosphate concentration is within its target range, even if the pH is outside of its target range.

In a preferred embodiment, the computer is programmed as follows: if the phosphate content is at the upper end of its target range, or even if it exceeds its target range, chemical will not be fed, because the blowdown of the system will eliminate the excess phosphate; if phosphate is directly on target, the system will feed phosphate at a rate so as to maintain this optimum value; and if the phosphate content is below the optimum amount the feed rate will be increased. When the phosphate content is below the optimum amount, the computer will be further programmed to determine the amount of each phosphate specie present in the boiler system. For example, if disodium phosphate and trisodium phosphate are the two phosphate species being used to control the water chemistry, the computer will determine how much disodium phosphate is present and how much trisodium phosphate is present. The computer will compare the actual amount of each phosphate specie with the target amount for each phosphate specie, and feed only the specie which is deficient to bring the total phosphate content within range. In some cases both species will be deficient and both will be fed.

Similarly, the computer can be programmed to alter the phosphate feed rate only if the pH is off target, if either pH or phosphate is off target, or only if both the pH and the phosphate are off target.

The computer or other controller adjusts the feed rate of chemicals into the system by controlling one or more chemical feed pumps. Signals are sent from the computer to the feed pump(s) by any suitable wiring means known in the art. Each feed pump is attached to a chemical feed tank, and controls the rate at which the water treatment chemical housed in the feed tank is introduced to the boiler based upon the signal received from the computer. Although the preferred embodiment of the present invention contemplates the use of two chemical feed tanks and two feed pumps which operate independently of each other, it is equally within the scope of the invention to employ any number of pumps and tanks. Any suitable type of feed pump can be used. For example, one could use an AC driven pump in which the stroke amount, i.e., the amount of chemical discharged over a given time, can be altered. Alternatively, a DC driven pump having a constant stroke value but a variable speed motor can be used; it is believed that the DC pump may provide for a more accurate feeding of the chemical(s).

There are several other parameters which may be taken into account in monitoring and controlling a boiler system; these parameters are also pre-programmed into the computer, based upon the individual characteristics of the boiler system being treated. In addition to the target box for sodium to phosphate ratio, other operating parameters include, inter alia, the types of chemicals being fed into the system, the types of feed pumps being used, how the pumps control the rate of the chemical feed, how often pump rates are adjusted, the volume of the boiler system being monitored and/or controlled, feedwater flow rate variations, boiler blowdown, steaming rate, boiler volume and residence time, and the desired phosphate and pH ranges.

Another factor to be determined by the user is the frequency with which the sodium to phosphate ratio will be calculated. If both the phosphate and the pH readings are constantly monitored, the sodium to phosphate ratio could be determined at almost any time. It is more typical, and preferred, however, to program the computer to calculate sodium to phosphate ratio and provide for pump adjustments at designated intervals, rather than on a continous basis. Ideally, the computer will be programmed to allow for some lag time between chemical addition—that is, some time for the boiler system to respond to the water treatment chemicals added in response to a previous sodium to phosphate ratio calculation—before an additional calculation/addition is performed.

As stated above, the phosphate concentration of the system is determined via FIA. FIA methods and apparatus require the continuous flow of a sample stream which mixes with a continously flowing reagent stream(s) to form a color reaction mixture product which is read on a colorimeter. The FIA methodology is typically carried out in an apparatus comprising a closed system in which the sample and reagent stream(s) are carried in conduit means consisting of tubing of suitable dimensions and materials. The sample stream is propelled to the FIA apparatus by the pressure of the boiler system. Within the FIA apparatus, the continuous movement of the reagent stream(s), as well as the combined sample/ reagent stream, or reaction mixture, is produced by a positive pressure accomplished by any suitable means, for example pumping means, such as a peristaltic pump, or a pressurized system in which compressed air or an inert gas such as nitrogen is used to propel the sample/reagent stream through the tubing and other apparatus means used to carry out the method. A pressurized system using, compressed air is preferred. Pressure is also maintained by the use of pressure regulators, restrictor coils with reduced internal diameters, back pressure loops and/or semi-permeable membranes through which the reaction mixture passes to remove entrained air, in combination with the pressurized gas. The pressure in the system should be between 2 and 10 psig, preferably between 4 and 6 psig.

The flow injection analysis methods generally involve the steps of: a) establishing a filtered sample stream from said system from which sample units may be selected at designated intervals; b) bringing together and admixing on a continuous basis two reagent composition streams so as to form a basic flow injection analysis stream, the two reagent composition streams comprising a color-forming reagent, said color-forming reagent comprising an inorganic acid and molybdenum (V and VI), and a reducing agent and preservative composition; c) interrupting the flow of the reducing, agent and preservative composition reagent stream and substituting therefor the filtered sample stream of step (a) for sufficient time to select a sample unit, thereby allowing mixing, with the color-forming reagent to form a reaction mixture; d) restoring the flow of reducing agent and preservative composition stream; e) heating the reaction mixture to approximately 40° C. for a sufficient time to effect the reaction of substantially all of the phosphate in the sample with the molybdenum V and VI to form a color complex, and thereafter allowing, the reducing agent to partially reduce the molybdenum V and VI so that it has an average oxidation state between 5 and 6; f) passing the reaction mixture containing the color complex through a colorimeter having, a 600–850 nanometer (nm) filter and reading a signal produced thereby; and g) calculating the concentration of phosphate in the sample from the signal and previously available standardized data; wherein all of the above steps are carried out under a pressure of from 2–10 psig.

Alternatively, steps b), c) and d) above can be substituted with the steps of: at one said designated interval, selecting a sample unit and injecting it as a discrete unit into a continuously flowing reducing agent stream comprising a reducing, agent and preservative composition, so that the reducing agent stream is present in front of and behind said sample unit; and continuously injecting a reducing agent and a color-forming, reagent stream comprising an inorganic acid and molybdenum V and VI into the sample unit in such a manner that the sample unit and color-forming reagent are thoroughly admixed while bounded in front and behind by said reducing agent stream forming a reaction mixture.

The tubing which is used to carry the sample stream, as well as the reagent composition streams and reaction mixture stream, must be composed of a material which is able to withstand the rather harsh conditions to which it is continually subjected, such as elevated temperatures and pressures and strong reagents, while maintaining dimensional uniformity within very strict tolerances, which is essential for assuring consistency and reproducibility of the analytical results over a long period of time. Any suitable inert material can be used, preferably a polymer material such as polypropylene, polytetrafluoroethylene (PTFE), or polyetheretherketone (PEEK); PEEK is preferred for use in the apparatus of the present invention.

The size of the tubing is selected so as to accomplish a desired flow rate with respect to a sample size within a desired range, which makes economic use of the required reagents and affords an adequate reaction time. In the methods and apparatus of the present invention, it has been found useful to employ tubing having, an internal diameter of from 0.0125 to 0.1000 centimeters (cm), with an internal diameter of 0.0500 cm (=0.02 inches) being, preferred. By using tubing, having the preferred 0.0500 cm internal diameter, a flow rate throughout the flow injection system of between 0.13 and 0.18 milliliters per minute (mL/min), preferably 0.15 mL/min, is maintained. With such a flow rate, the sample unit size may vary between 10 and 150 microliters ($\mu L$), preferably between 20 and 125 $\mu L$, and most preferably 20 $\mu L$.

Although boiler water generally should be relatively free from fine solids or other particulate matter, sample filtration may be desired to separate suspended material and to prevent plugging of the FIA instrument. If filtration is used, it should be established after the take-off valve and before the sample stream enters the FIA apparatus. Bypass membrane filtration is preferred, with tangential entry of bypass being desirable for on-line sample filtration because membrane fouling is slowed by the cleaning action of the sample stream. Commercial filtering systems which are suitable include the Minitan-S filter assembly from Millipore Corp., Bedford, Mass., and the Collins Swirlclean Bypass Filter from Collins Products Company, Livingston, Tex. Any filter material or device which will remove the suspended fine solids from the sample stream is suitable; it has been found that good results are achieved when particles of 0.45 microns and larger are removed.

A conduit running from the first take-off valve and optionally through a filtering system is attached to the FIA apparatus via a three-way valve or some other standard valve means known in the art. Use of a three-way valve allows for a continuous flow of fresh sample to run from the take-off valve either to waste or, by switching the three-way valve, to the remainder of the FIA apparatus.

Because the sample stream coming from the boiler is continuously flowing, however, it is necessary to establish a way by which sample units may be selected at designated intervals. This is suitably carried out using a selector valve together with an injection valve, either alternatively or in addition to the three-way valve. Both the selector valve and injection valve are of known design and allow the sample stream to flow in a continuous manner through the selector and injection valves to waste, but not through any other part of the flow injection analysis system. In addition to assuring that a fresh sample unit is provided whenever a sample is to be analyzed, the selector valve also functions to permit the introduction of standards and distilled water into the basic flow injection analysis stream. It will be appreciated that other devices may be substituted for the selector valve.

Sample units for evaluation by the flow injection system are selected at designated intervals as frequently or infrequently as the operator desires. The designated intervals are predetermined based on the number of samples that it is desired to test within a given period of time, and are usually pre-programmed into the computer or similar device which controls the operation of the entire flow injection analysis system. During conventional operation, the selector valve will be set so that the sample stream enters the selector valve and then goes on to the injection valve, and from there to waste. On command from the computer or other control device, or even manually, the injection valve directs the sample stream through a sample loop of tubing which is of the appropriate dimensions to give the desired sample size, most preferably 20 µL.

The sample loop is preferably in the separate device termed the injection valve, which has as its function the injection of the sample unit into the continuously flowing, reagent stream. The injection of the sample unit into a reagent stream may take place in at least two different ways which, while accomplished by different means, are conceptually the same. One such means is a mixing valve, which has two or more inlet ports and a single outlet port. Within the valve assembly, means controlled by the operation of a solenoid allow measured quantities of the contents of a tube leading to one of the inlet ports to pass through the valve assembly and out the outlet port. The solenoid then closes that inlet port and opens a second inlet port, where again a measured quantity of the contents of a tube leading to the second inlet port are allowed to pass through the valve assembly and out the outlet port. By alternating the opening and closing of these inlet ports, e.g., once a second, a thorough mixing of the contents of the two tubes entering the inlet ports is achieved. A solenoid operated mixing, valve of the type sold by Bio-Chem Valve Corporation or General Valve Company has the advantages of efficiently, reliability, and economy. Such mixing, valves feature low power consumption, isolated solenoids, high cycle life, low internal volume, fast response time, Teflon wetted parts, and valve seat travels adjusted for accurate fluid sampling. The mixing valve can mix together the proper ratio of reagents and samples by switching from one stream to another rapid succession, resulting in a well mixed solution with faster reaction times and sharper peak shape from the colorimeter.

When a mixing valve is used for the FIA determination of orthophosphate content, it functions as follows. The two reagent composition streams which form the basic flow injection analysis stream are brought together and admixed at the mixing valve. These two reagent composition streams are: (a) the color-forming, reagent comprising an inorganic acid and molybdenum (V and VI); and (b) the reducing agent which optionally contains a preservative composition. Either the timing of the solenoid which controls the amount of each reagent stream leaving the outlet port, or the concentrations of the reagent compositions themselves, may be adjusted so as to predetermine the ratio of the reagent concentrations in the basic flow injection analysis stream. These can be set as desired, depending on the makeup and stoichiometry of the reagent composition streams. For example, where concentrated sulfuric acid is used in the color-forming, reagent and ascorbic acid is used as the reducing agent, the time and/or concentrations are adjusted to provide a 1:1 molar ratio of the reagents.

When a sample unit is to be analyzed, the selector and injection valves are set and activated so that a sample unit travels through a tube to a third inlet port of the mixing valve described above, where it enters the mixing valve. At the same time, however, the inlet port for the reducing agent and preservative composition is closed, so that the sample unit is, in effect, substituted therefor, and as a consequence, the sample unit becomes admixed with the color-forming reagent which is still entering the mixing, valve. After the sample unit has completely passed through the mixing valve, its inlet port is closed and that for the reducing agent and preservative is reopened. As a consequence of the above actions, it will also be seen that the reducing agent and preservative reagent composition is present in front of and behind the sample unit in the basic flow injection analysis stream.

Alternatively, a three-way valve connected by tubing directly to the mixing valve, through which sample continuously flows to waste through one of the ports of the three-way valve, can be used in place of the selector and injector valves. By means of such a valve, it is possible to have a continuous flow of fresh sample, and then by switching the three-way valve, provide for direct flow of a sample unit to the mixing, valve, the unit size being determined by the length of time that the three-way valve remains open for passage of sample.

Another means for accomplishing the injection of the sample unit into a reagent stream involves the use of a selector valve and an injection valve as described above together with a T-connector. As with the mixing valve embodiment, during the stage of readiness for receiving a sample unit, the two reagent streams are mixed together on a continuous basis, but by means of being brought together at the T-connector rather than through a mixing valve. When a sample unit is to be analyzed, the injection valve is activated and the sample unit is injected into the reducing agent and preservative composition reagent stream, which also passes through the injection valve on a continuous basis. As a consequence, the reducing, agent stream is present in front of and behind said sample unit, viewed as a continuously flowing stream, just as with the mixing valve embodiment described further above. The reducing agent stream pushes the sample unit on ahead of it so that when the sample unit reaches the T-connector, only sample and color-forming reagent are admixed at the T-connector, just as with the mixing valve embodiment described further above.

In both embodiments described above, as the sample/color-forming reagent mixture passes through the remainder of the flow injection analysis system the color reaction mixture product is formed. Specifically, this colored product is a result of the reaction between orthophosphate and molybdenum. Orthophosphate and molybdenum VI will react to form a heteropoly yellow complex. Subsequent reduction of the yellow complex with a reducing agent, or the initial reaction of orthophosphate with molybdenum V, results in a heteropoly blue complex, which is the color product read by the colorimeter. During the course of this passage through the apparatus, the molybdate solution and reducing agent completely mix with the orthophosphate to form this heteropoly blue complex.

As stated above, one of the two reagent composition streams is a reducing agent stream which comprises a reducing agent and, optionally, a preservative composition. The reducing, agent acts to reduce the phosphomolybdate yellow complex to the heteropolymolybdate blue form. Any suitable reducing, agent known in the art can be used. A commonly employed reducing agent recognized for this purpose is ascorbic acid, and this is the preferred reducing agent for use in the methods of the present invention.

Decomposition of a reducing agent such as ascorbic acid will occur without the use of one or more preservatives. Such decomposition can be caused by dissolved oxygen in the boiler system, or by the presence of oxygen radicals. The presence of heavy metals may also catalyze such decomposition. Preservative agents for use with the reducing agents of the present invention, and which act as oxygen scavengers, include those recognized in the art as suitable for that purpose, e.g., ketones, such as methylethyl ketone or acetone, which is preferred, glycerol and glycol. They may be used alone or in combination.

Chelating agents which bind to heavy metals capable of catalyzing the decomposition of the reducing, agents may also be used in the preservative composition. Any chelating agent which will chelate metals which cause instability of the ascorbic acid, and which is otherwise compatible with the other elements present in the methods of the present invention, may be used. A preferred chelating agent is ethylenediaminetetraactic acid (EDTA) in any of its various salt forms, e.g., tetrasodium EDTA, edetate sodium, edetate disodium, edetate trisodium, and edetate calcium disodium. Disodium EDTA is preferred. Nitrilotriacetic acid may also be used, for example.

The amount of reducing agent, such as ascorbic acid, employed will be between 10 and 30 grams per liter (g/L), preferably between 15 and 20 g/L. The amount of preservative such as acetone employed will be between 45 and 55 milliliters per liter (mL/L), preferably 50 mL/L.

A preferred reducing agent and preservative composition for use in the method of the present invention has the following composition: 16.6 g ascorbic acid; 50 mL acetone; 7.6 mg disodium EDTA; in 1 L of deionized water. The disodium EDTA is conveniently added as 2 mL of Calgon Reagent R-5010 which is 0.001M EDTA and contains sufficient NaOH to solubilize the EDTA, as well as a very small quantity of a preservative.

The second of the two reagent composition streams is a color-forming reagent stream which comprises an inorganic acid and molybdenum (V and VI). This molybdenum color-forming reagent composition may be prepared in accordance with procedures known in the art. Alternatively, in the preferred method, a molybdate reagent for use in the methods of the present invention may be prepared simply by dissolving from 5 to 15 g, preferably 10 g of ammonium molybdate tetrahydrate [$(NH_4)_6Mo_7O_{24} \cdot 4H_2O$] in from 60 to 120 mL, preferably 102 mL of concentrated (95%) sulfuric acid ($H_2SO_4$). The solution may then be diluted to 1 L with deionized water to give the molybdenum (V and VI) reagent solution. When this reagent mixes with the reducing agent stream containing, e.g., ascorbic acid, the ascorbic acid partially reduces the molybdenum so that it has an average oxidation state between 5 and 6. The molybdenum blue color complex results.

The next step involves heating the reaction mixture. Heating the reaction mixture to a temperature not exceeding 40° C. catalyzes or facilitates the reaction of substantially all of the phosphate with the color-forming reagent. The time for this step to be completed will be from 10 to 25 minutes, usually from 15 to 20 minutes. A typical residence time for the completion of this step is 16 minutes. The device most convenient for carrying out this step is a simple reaction coil, e.g., one coil of tubing 1000 cm in length and 0.0500 cm (=0.02 inches) internal diameter encased in an aluminum block heater. Other devices may be substituted for the reaction coil; any device known in the art can be used. Because the heating coil contributes to the mixing, of the reagents and sample, if using a heating, device without a coil an in-line mixer situated before the heating device could be employed to ensure adequate mixing of the sample and reagents.

Even though the reaction temperatures for the step described above are below the 100° C. boiling point of water, and it is therefore unlikely that significant amounts of dissolved air gases (oxygen and nitrogen) will come out of solution, it is preferred to employ an air filter which will remove any such bubbles of gas which may unexpectedly appear. The evolution of gas bubbles can cause unacceptable detector "noise" when the reaction mixture containing the color complex is passed through the colorimeter for reading. The air filter is conveniently a semipermeable membrane through which the reaction mixture is passed to remove any extraneous gases which have formed. Such air filters are well known in the art.

The next step in the flow injection analysis determination of phosphate content involves passing the reaction mixture containing the color complex through a colorimeter. This is typically a flow-through cell spectrophotometer equipped with a filter which permits monitoring of the heteropoly blue complex within a wavelength range of from 600 to 850 nm. A 650 nm filter is usually, and preferably, employed. The path length for the flow-through colorimeter cell is from 0.5 to 2 cm, but is preferably 1 cm in length.

The last step of the flow injection analysis methods as used in the present invention involves taking the information obtained from the colorimeter reading in the preceding step and, together with standardized data, calculating the concentration of total inorganic phosphate contained in the boiler system from which the sample was obtained. It is desirable to employ standards and routinely test these so as to obtain and have readily available 2-point or 3-point standardization data. It is most convenient to employ a computer to process all of this data and calculate the phosphate content. The signal from the colorimeter may be sent directly to such a computer that permits a very rapid and automatic readout of the concentration of total orthophosphate in the boiler system on an ongoing and regular basis at the desired intervals. The FIA apparatus of the present invention preferably is equipped with its own computer which is programmed to both determine phosphate content and to also receive the output signal coming from the pH meter. The FIA computer will further be programmed to calculate the sodium to phosphate ratio from the pH value and phosphate concentration. In addition, the computer will be attached to and control the feed rate of the chemical feed pumps.

In another embodiment of the present invention, the FIA methodology includes the step of determining pH. In this embodiment, the FIA apparatus itself is equipped with a pH probe. The pH probe is employed at some point in the system after filtration of the sample, but before the addition of any reagents. Preferably, a solid state pH probe approximately 0.125 inches in size will be placed within the tubing of the FIA apparatus. Other pH probes, such as those used in chromatography, familiar to those skilled in the art can also be used. A three-way valve will be employed, through which travels two streams—the sample stream and a buffer solution used to calibrate the pH meter. Switching the three-way valve determines which of the streams will pass through the rest of the FIA apparatus. The pH probe is connected directly to the FIA's computer, which will directly read the pH probe. Accordingly, in this embodiment, the computer will be programmed to determine both the pH value and the phosphate concentration as described above, use these values to determine the sodium to phosphate ratio, and finally control the feed pumps as needed to achieve or maintain this ratio.

FIG. 1 of the drawings depicts a typical analyzer apparatus for carrying out the methods of the present invention.

The solid lines depict conduit means, i.e. tubing, while the dotted lines represent wires or other suitable means by which signals can be transmitted. The depiction is not drawn to scale.

A sample stream 12 runs continuously from a boiler system 10. The sample stream 12 flows to waste 14. A first take-off valve 16 is positioned in the sample stream 12 to remove a portion of the sample stream 12 for determination of orthophosphate content. This portion of the sample stream is carried through tubing 18, to an FIA apparatus 20. The FIA apparatus 20 is equipped with a computer. When a sample is selected, the sample stream 12 passes through the FIA apparatus 20 to waste 21.

A second take-off valve 22 is also positioned in the sample stream 12 to remove a portion of the sample stream for determination of pH. This portion of the sample stream is carried through tubing 24 to a pH meter 26. The sample stream passes through the pH meter 26 to waste 25.

Out-put signals from the pH meter 26 are sent via line 62 to the computer of the FIA apparatus 20. The computer in the FIA apparatus 20 in turn controls two pumps 34 and 36 via line 38, which splits into lines 40 and 42 which run to pumps 34 and 36 respectively.

The first pump 34 is connected via conduit 44 to a first chemical storage tank 46. The second pump 36 is connected via conduit 50 to a second chemical storage tank 48. The first pump 34 controls the flow rate of a first water treatment chemical 45 from the first storage tank 46 to a T-connector 56 via conduit 52. Likewise, the second pump 36 controls the flow rate of a second water treatment chemical 47 from the second storage tank 48 to T-connector 56 via conduit 54. The two conduits 52 and 54 leading from the two pumps 34 and 36 are joined at T-connector 56. The first and second water treatment chemicals 45 and 47 are then carried via conduit 58 to the boiler system 10.

Figure 2:
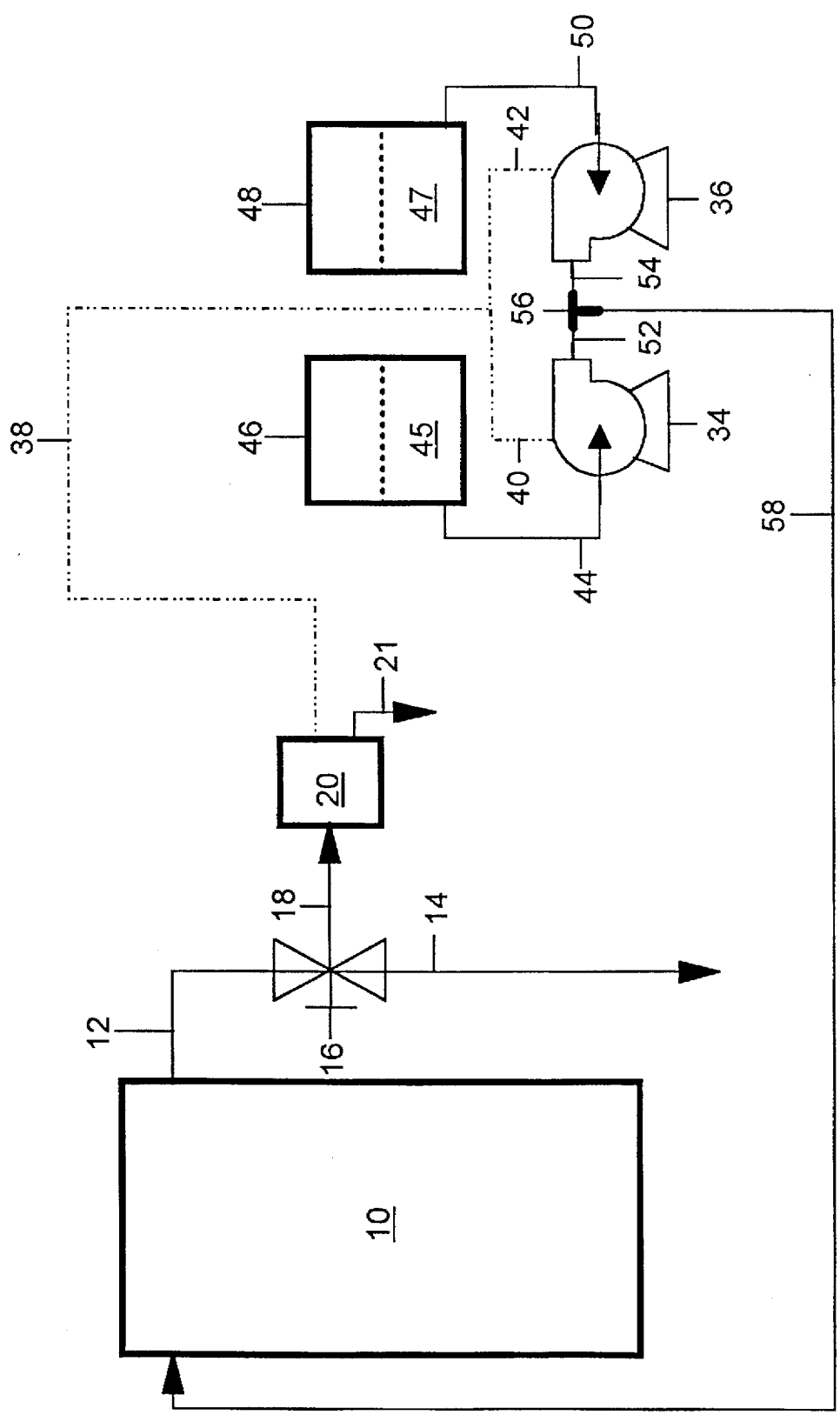
FIG. 2 is a schematic diagram of another embodiment of the apparatus according to the present invention wherein the FIA apparatus contains its own pH meter.

FIG. 2 depicts another embodiment of the present invention in which the FIA apparatus 20 also contains a pH meter. The remainder of the apparatus and its function are as described further above for FIG. 1.

EXAMPLES

The following examples are set forth to illustrate the invention and should not be construed as limiting the invention in any way.

Example I

A simulated boiler system was established with the following conditions and control parameters, as if being, operated at a pressure of 900 psig:

System volume: 35 gallons

Boiler water phosphate target: 25 ppm total phosphate

Boiler water pH target: 10.07

Two chemicals being fed: monosodium phosphate and trisodium phosphate

Half-life*: between about 7–8 hours

High purity water $N_2$ purged system

*Half-life refers to the amount of time it would take for the phosphate content of the system to be reduced by half if no additional phosphate was added.

Monitor of phosphate content and pH and control of chemical feed was achieved by using an FIA apparatus equipped with a pH monitor and computer, as described above. To determine the pH and phosphate content of the system, a filtered sample stream ran to the FIA apparatus and passed through the pH meter. A signal representing the pH was sent to the computer on a continuous basis. The sample stream then ran to a selector valve. At designated intervals, the selector valve directed the sample stream through a 20 µl sample loop in an injection valve. The injection valve switched the sample in-line and the ascorbic acid reagent, which functioned as a carrier, pushed the sample ahead. The sample mixed with the molybdate reagent at a 90° angle T-connector. The ascorbic acid and molybdate reagents were prepared in the preferred manner as described above. From the T-connector, the sample/reagent mixture entered a 25 foot, 0.02 inch internal diameter heating coil at about 40° C. Travel time from injection of the sample through the heating coil was approximately 10 minutes. From the heating coil, the sample/reagent mixture passed through an air filter to remove any extraneous bubbles which may have formed. Next the sample/reagent mixture flowed through a colorimeter with a 1 cm path length and 650 mn filter. The signal was sent to the computer which calculated the phosphate content from standardized data obtained periodically by injecting orthophosphate standards. The computer then calculated the sodium to phosphate ratio from the pH valve and the phosphate content. Adjustments to the feed pumps were automatically made by the computer based on the sodium phosphate ratio. The test was run for 48 hours. The results are presented in FIGS. 3, 4, and 5.

Figure 3:
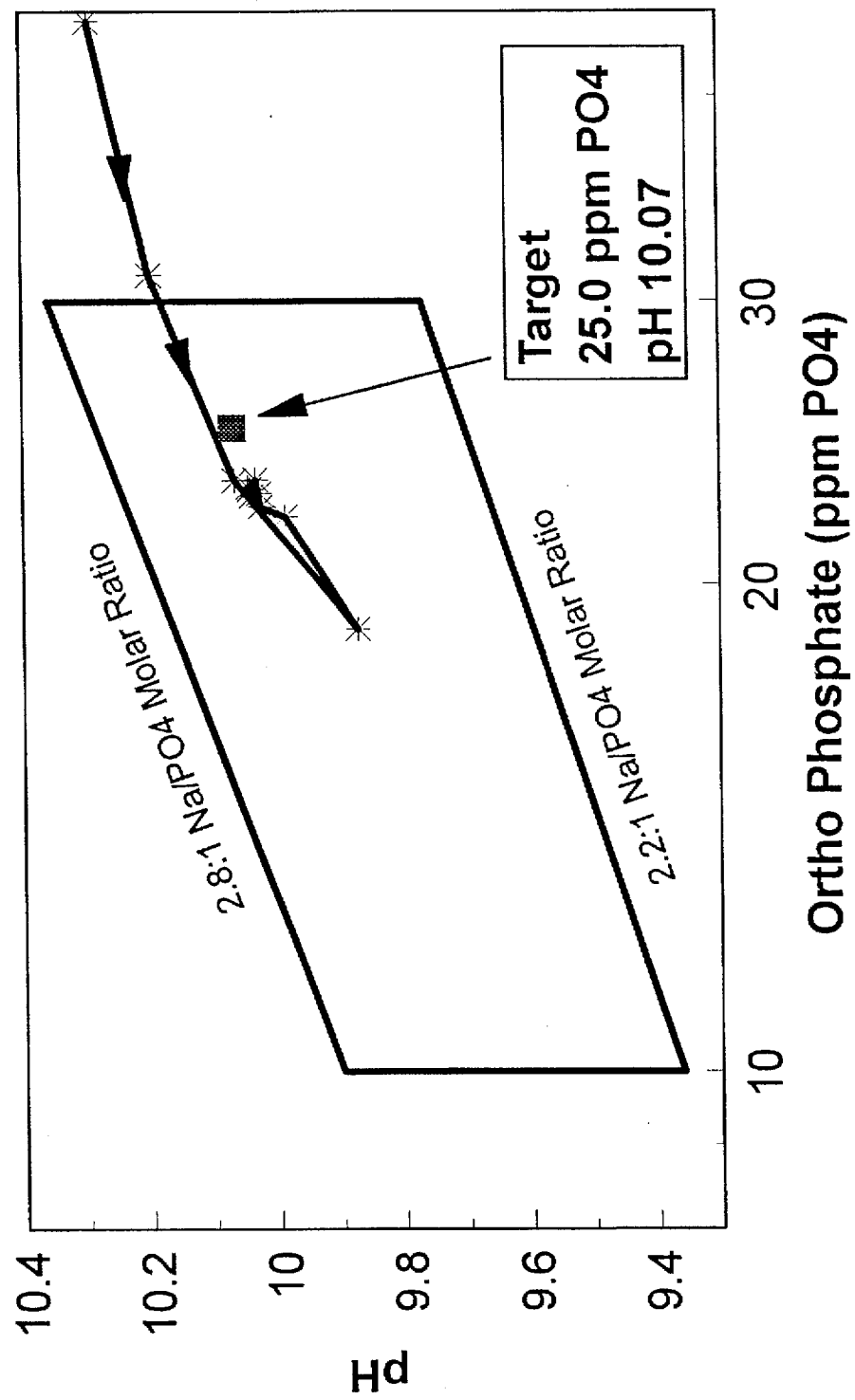
FIG. 3 is a graph showing, the relationship between phosphate concentration versus pH over 44 hours, as monitored and controlled by the method described in Example I.

FIG. 3 shows the relationship between pH and phosphate over 44 hours with the, asterisks representing the average values for these parameters taken over a 4 hour period.

Figure 4:
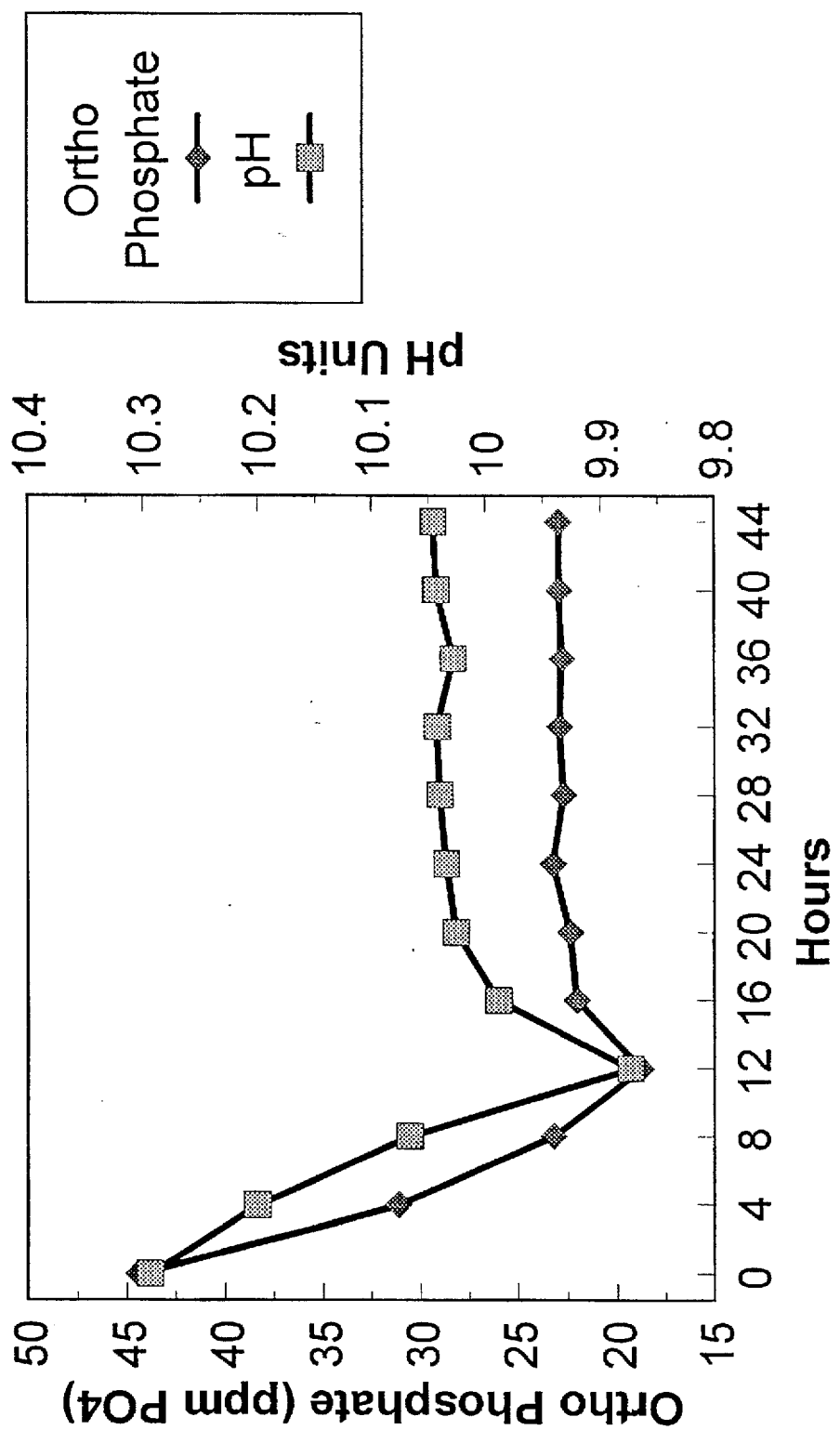
FIG. 4 is a graph showing the relationship between pH versus time and phosphate content versus time over 44 hours, as monitored and controlled by the method described in Example I.
Figure 5:
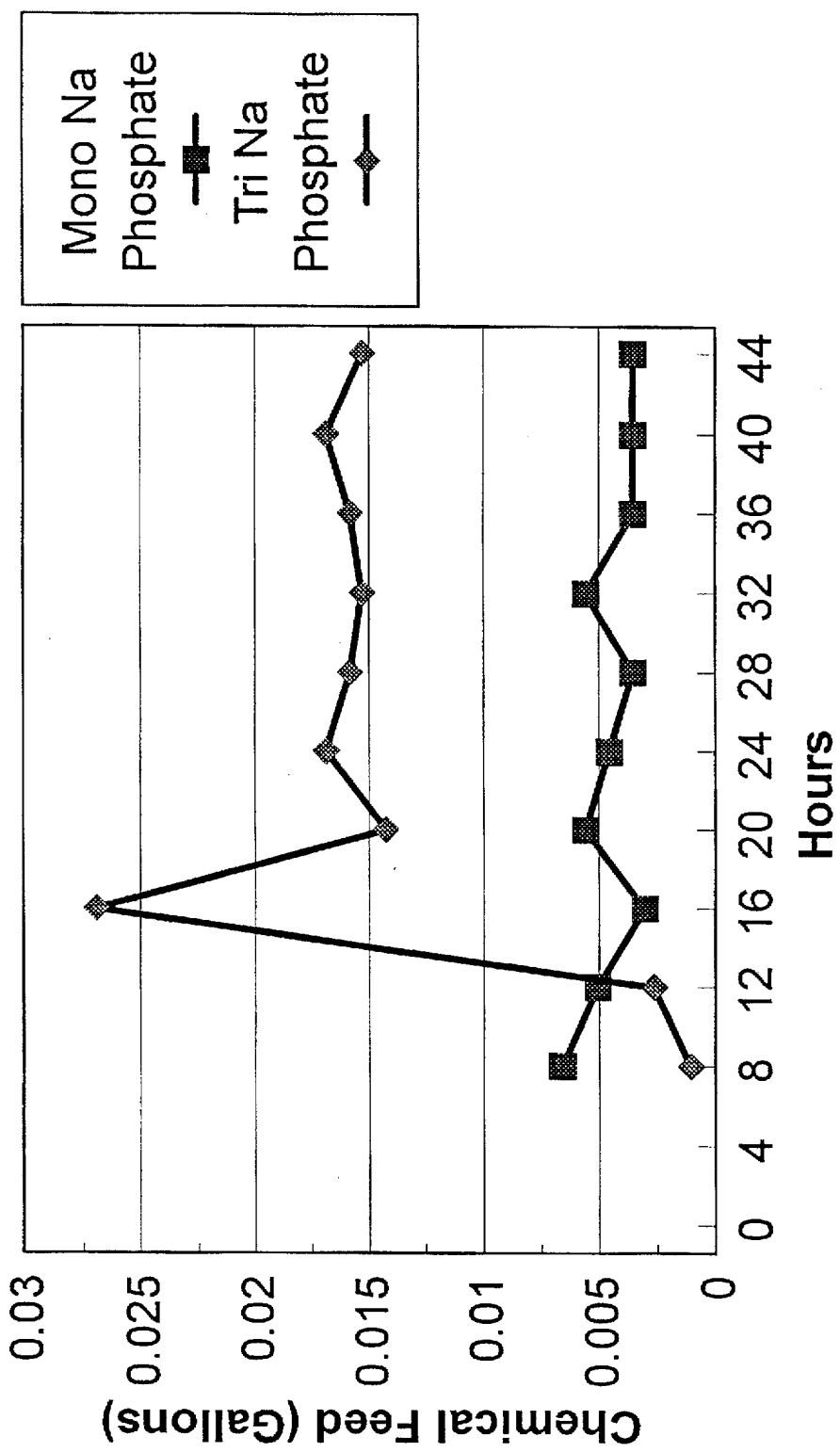
FIG. 5 is a graph showing, the relationship between mono and tri sodium phosphate feed versus time over 44 hours, as monitored and controlled by the method described in Example I.

The lines labeled "2.8:1" and "2.2:1" represent pH and phosphate values which correspond with these two sodium to phosphate ratios and define the molar ratio box. FIG. 4 separately plots pH and phosphate against time. As can be seen from these figures, the initial pH and phosphate content of the system were higher than the target level for these parameters. FIG. 5 plots chemical feed of the mono and tri sodium phosphate species over time. As can be seen from that figure, the computer fed a higher amount of monosodium phosphate initially to bring the pH within range, and a higher amount of trisodium phosphate when the pH dropped slightly below target (at about hour 12). Following that time, the computer maintained the system at or near the target values by adding trisodium phosphate to monosodium phosphate in a ratio of approximately 3:1. From the initial reading, it took the system approximately 4 hours to get within the target box, and approximately 12 hours after that to get at or near the target.

Example II

Figure 6:
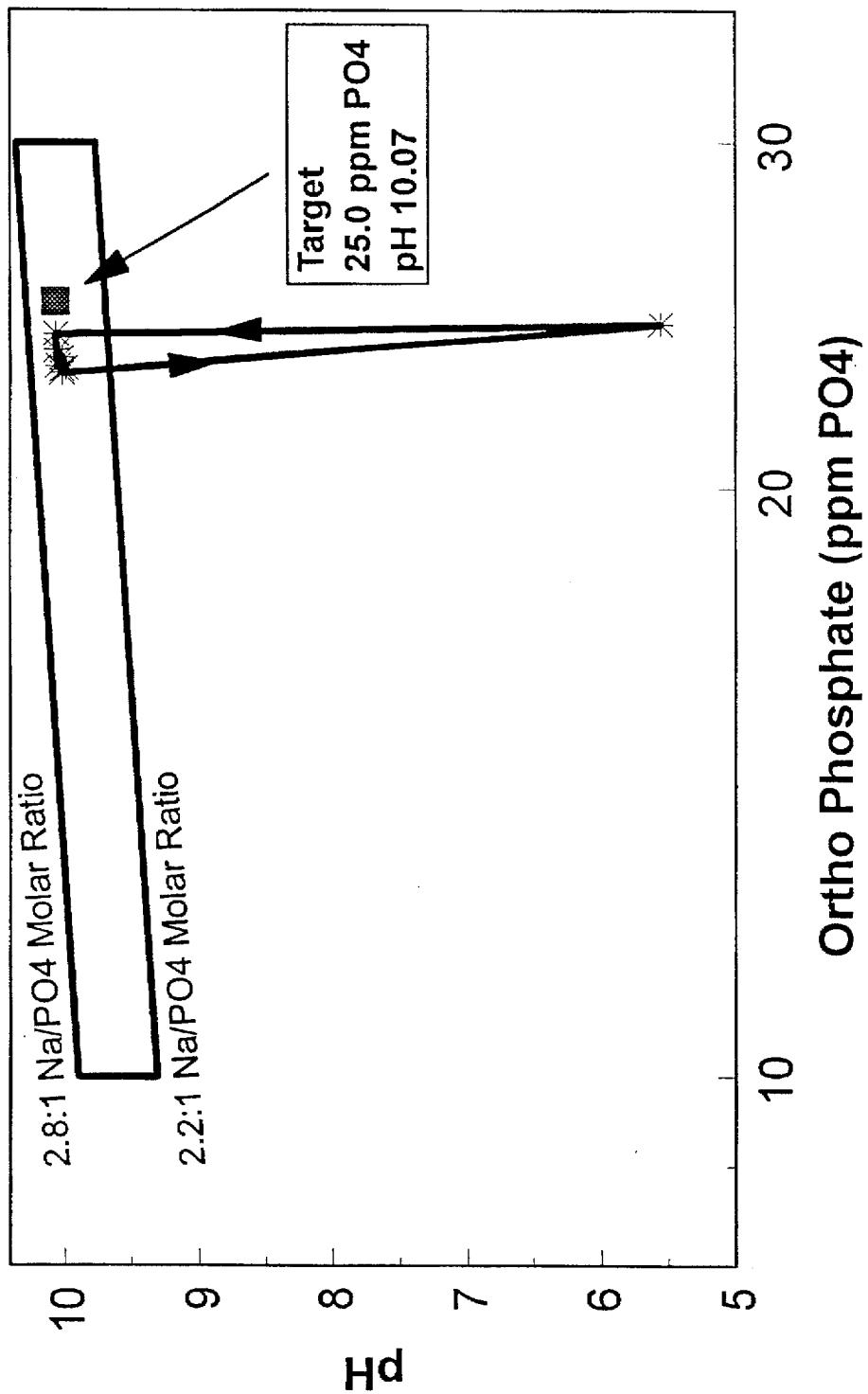
FIG. 6 is a graph showing the relationship between phosphate concentration versus pH over 28 hours, as monitored and controlled by the method described in Example II.
Figure 7:
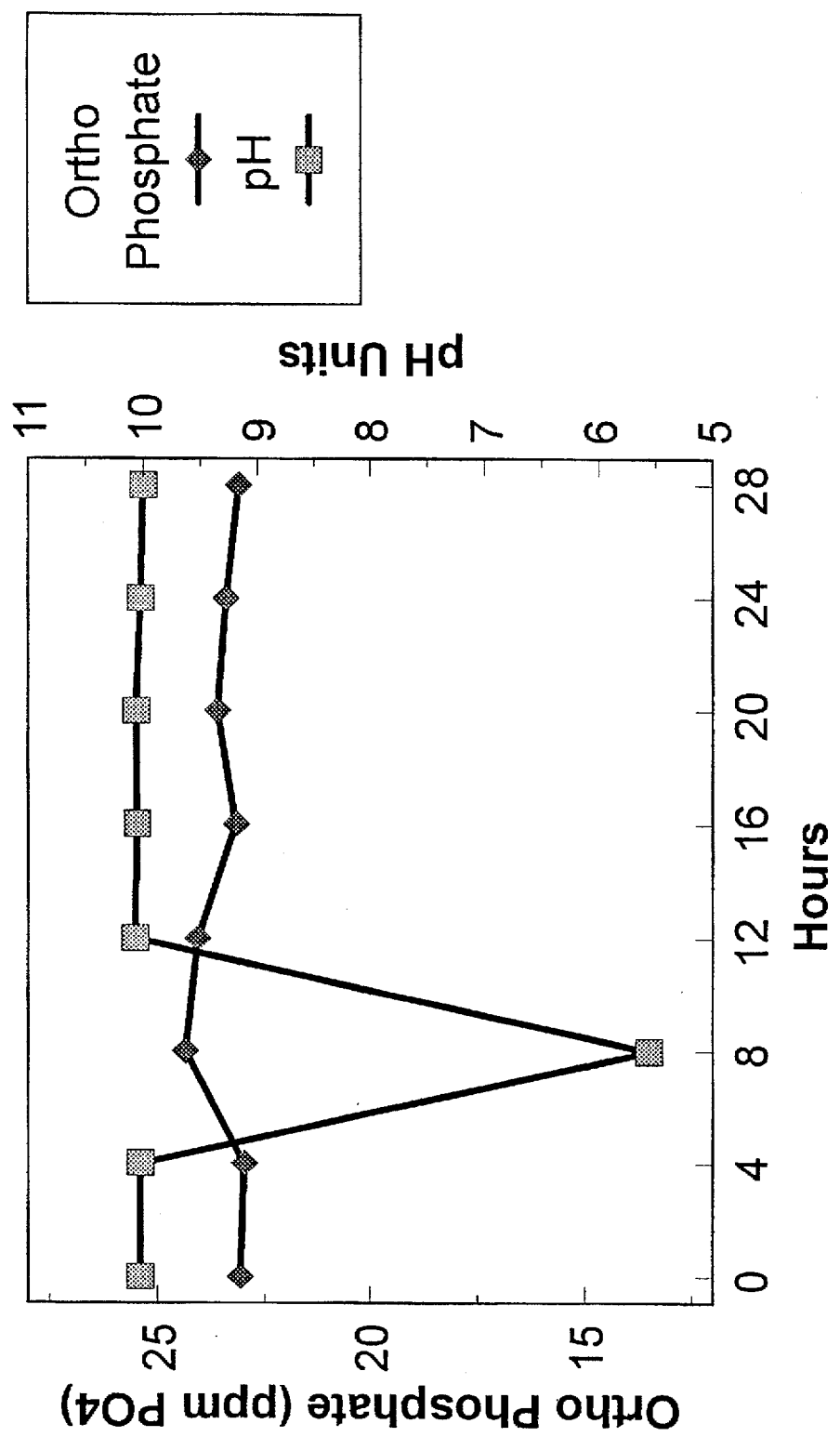
FIG. 7 is a graph showing the relationship between pH versus time and phosphate content versus time over 28 hours, as monitored and controlled by the method described in Example II.
Figure 8:
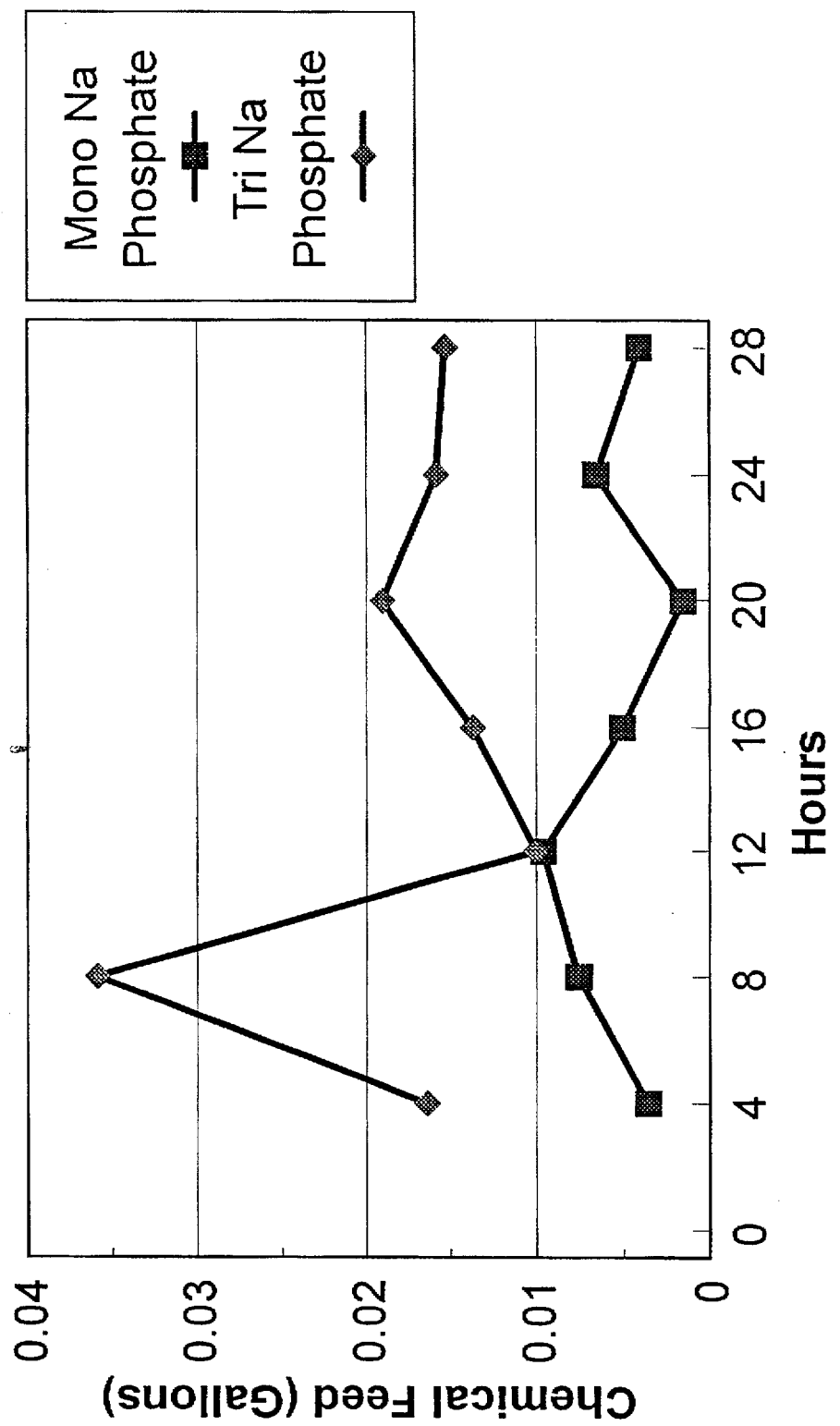
FIG. 8 is a graph showing the relationship between mono and tri sodium phosphate feed versus time over 28 hours, as monitored and controlled by the method described in Example II.

Example I was repeated. Prior to beginning the test, sulphuric acid was intentionally added to the system to bring pH below target. Through the FIA analysis it was confirmed that pH was below target, and also that the phosphate content was within target. The results are presented in FIGS. 6, 7 and 8. As can be seen in FIG. 8, which plots chemical feed of the mono and tri sodium phosphate species over time, the computer initially fed trisodium phosphate to bring the pH up within range. Once target values were reached for both pH and phosphate, trisodium phosphate and monosodium phosphate were fed to the system in a ratio of approximately 3:1. As can be seen from FIGS. 6 and 7, it took the system approximately 4 hours to get within the target box and approximately 8 hours to get at or near the target.

Example III

Figure 9:
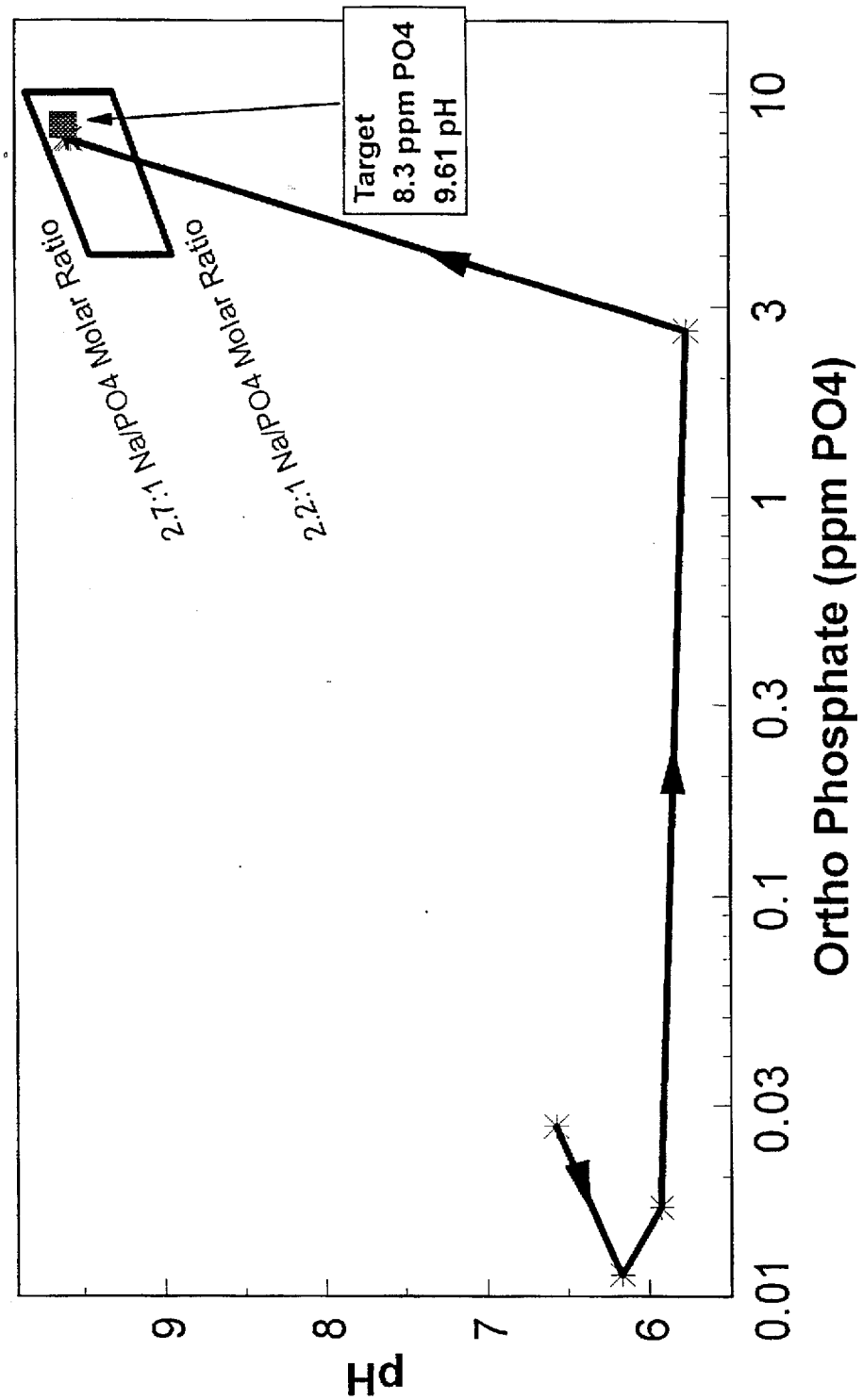
FIG. 9 is a graph showing, the relationship between pH versus phosphate content over 28 hours, as monitored and controlled by the method described in Example III.
Figure 10:
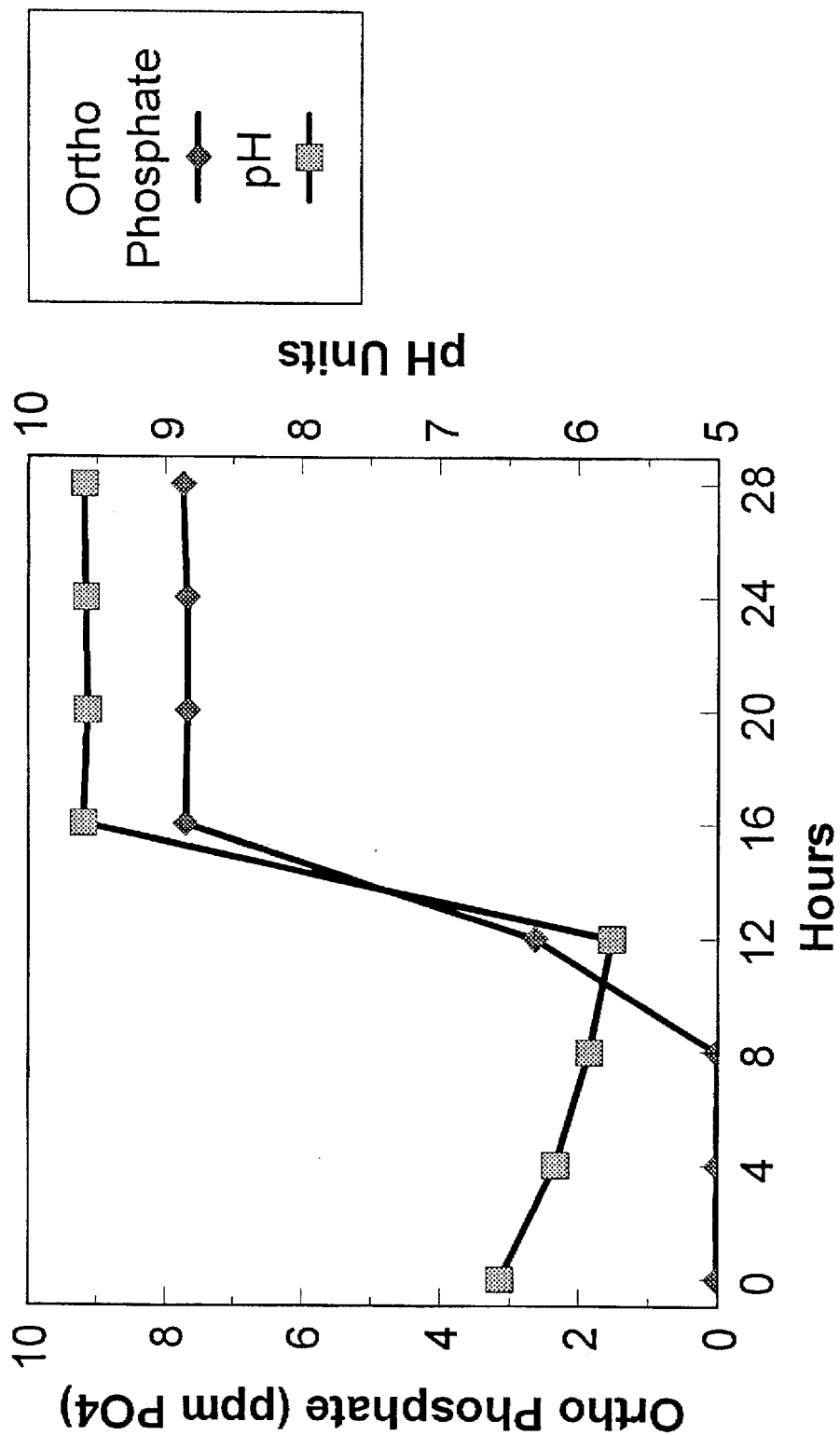
FIG. 10 is a graph showing, the relationship between phosphate content versus time and pH over 28 hours, as monitored and controlled by the method described in Example III.
Figure 11:
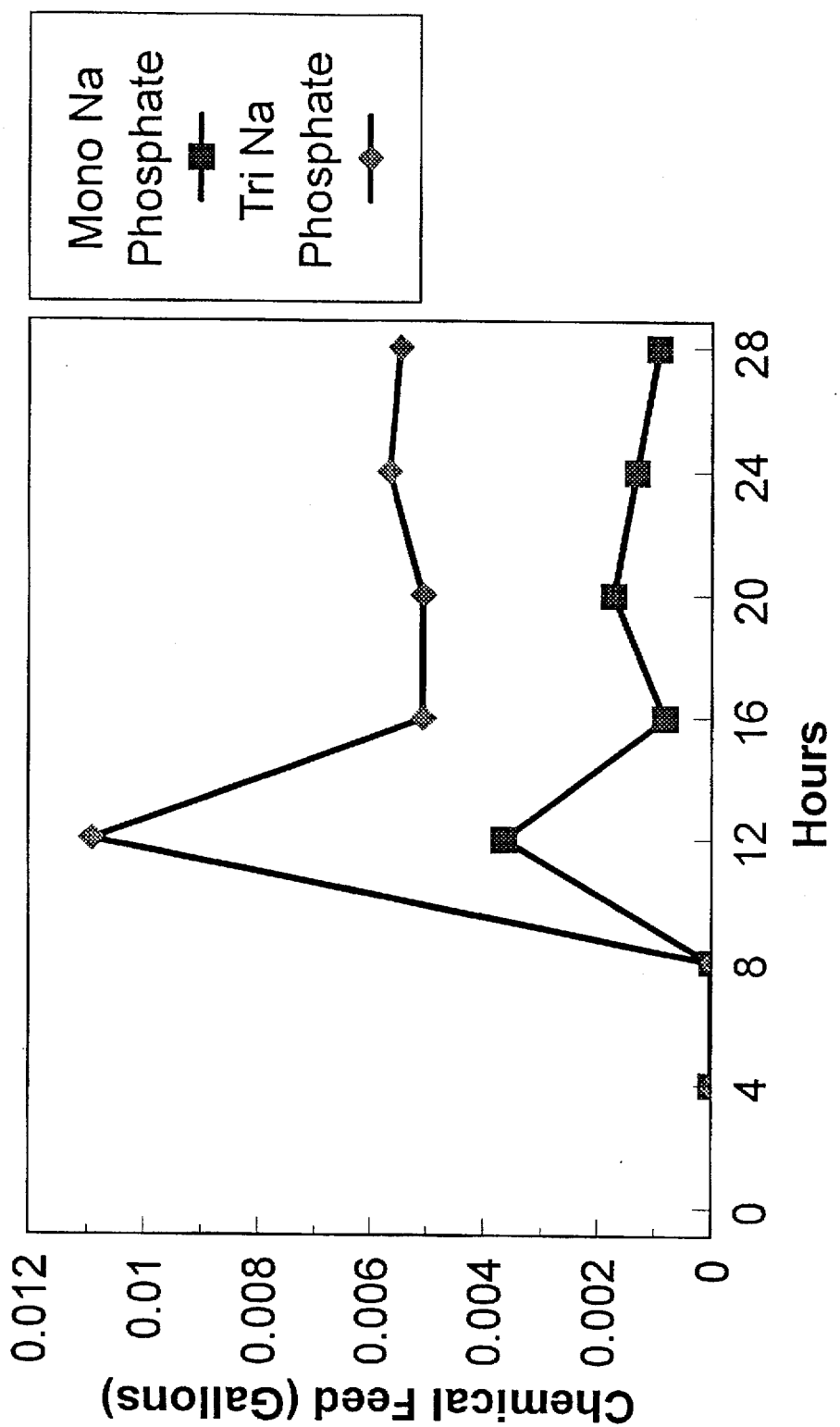
FIG. 11 is a graph showing the relationship between mono and tri sodium phosphate feed versus time over 28 hours, as monitored and controlled by the method described in Example III.

A boiler system was established with the following conditions and control parameters, as if being operated at a pressure of 1500 psig:

System volume: 35 gallons
Boiler water phosphate target: 8.3 ppm total phosphate
Boiler water pH target: 9.61
Two chemicals being fed: monosodium phosphate and trisodium phosphate
Half-life: between about 7–8 hours
High purity water
$N_2$ purged system The methods of Example I were repeated in a system operating under the above parameters. The results are presented in FIGS. 9, 10 and 11. As was determined by the FIA apparatus, the system had initial conditions of low phosphate content and low pH. To compensate for these conditions, the computer significantly increased the feed of both phosphate species to bring pH and phosphate within the target box, as is illustrated in FIG. 11. Once target values were reached for both of these parameters, the computer fed trisodium phosphate and monosodium phosphate to the system in a ratio of approximately 3:1. As can be seen from FIGS. 9 and 10, it took the system approximately 16 hours to get at or near the target.

What is claimed is:

1. A method for monitoring and/or controlling pH, phosphate concentration and sodium to phosphate ratio in a boiler system using captive alkalinity, comprising the steps of:
   a) determining the phosphate concentration of said system by using flow injection analysis (FIA);
   b) substantially simultaneously determining the pH of said system by a pH meter;
   c) transmitting a value corresponding to the determined phosphate concentration of the system and a value corresponding to the determined pH of the system directly to one of a computer or controller;
   d) calculating the sodium to phosphate ratio by one of said computer or said controller based upon the values corresponding to the determined phosphate concentration of the system and the determined pH of the system; and
   e) automatically controlling the feed rate of at least one water treatment chemical being added to said system based upon the calculated sodium to phosphate ratio and the values corresponding to the determined phosphate concentration of the system and the determined pH of the system so as to maintain the pH, phosphate concentration and sodium to phosphate ratio within desired ranges through one of said computer or said controller.

2. The method of claim 1 wherein the step of determining the phosphate concentration of said system using FIA further includes the steps of:
   a) establishing a filtered sample stream from said system from which sample units may be selected at designated intervals;
   b) bringing together and admixing on a continuous basis two reagent composition streams so as to form a basic flow injection analysis stream, the two reagent composition streams comprising a color-forming reagent, said color-forming reagent comprising an inorganic acid and a molybdenum (V and VI), and a reducing agent and preservative composition;
   c) interrupting the flow of the reducing, agent and preservative composition reagent stream and substituting therefor the filtered sample stream of step (a) for sufficient time to select a sample unit, thereby allowing mixing with the color-forming reagent to form a reaction mixture;
   d) restoring the flow of reducing agent and preservative composition stream;
   e) heating the reaction mixture to approximately 40° C. for a sufficient time to effect the reaction of substantially all of the phosphate in the sample with the molybdenum V and VI to form a color complex, and thereafter allowing the reducing agent to partially reduce the molybdenum V and VI so that it has an average oxidation state between 5 and 6;
   f) passing the reaction mixture containing the color complex through a colorimeter having a 600–850 nanometer (nm) filter and reading a signal produced thereby; and
   g) calculating the concentration of phosphate in the sample from the signal and previously available standardized data; wherein all of the above steps are carried out under a pressure of from 2–10 psig.

3. The method of claim 1 wherein the step of determining the phosphate concentration of said system using FIA further includes the steps of:
   a) establishing a filtered sample stream from said system from which sample units may be selected at designated intervals;
   b) at one said designated interval, selecting a sample unit and injecting it as a discrete unit into a continuously flowing reducing agent stream comprising a reducing agent and preservative composition, so that the reducing agent stream is present in front of and behind said sample unit;
   c) continuously injecting a reducing agent and a color-forming reagent stream comprising an inorganic acid and molybdenum V and VI into the sample unit in such a manner that the sample unit and color-forming, reagent are thoroughly admixed while bounded in front and behind by said reducing agent stream forming a reaction mixture;
   d) heating the reaction mixture to approximately 40° C. for a sufficient time to effect the reaction of substantially all of the phosphate in the sample with the molybdenum V and VI to form a color complex, and thereafter allowing the reducing agent to partially reduce the molybdenum V and VI so that it has an average oxidation state between 5 and 6;
   e) passing the reaction mixture containing the color complex through a colorimeter having a 600–850 nm filter and reading a signal produced thereby; and
   f) calculating the concentration of phosphate in the sample from the signal and previously available standardized data; wherein all of the above steps are carried out under a pressure of from 2–10 psig.

4. The method of claim 1 wherein said water treatment chemical being added to said system is selected from the group consisting of sodium hydroxide, monosodium phosphate, disodium phosphate, trisodium phosphate, and phosphoric acid.

5. The method according to claim 1 wherein said water treatment chemicals being added to said system are disodium phosphate and trisodium phosphate.

6. An apparatus for monitoring and controlling pH, phosphate concentration and sodium to phosphate ratio in a boiler system operating on captive alkalinity, comprising:
   a) FIA means for determining the phosphate concentration of said system;
   b) means for substantially simultaneously determining the pH of said system;

c) means for transmitting a value corresponding to the determined phosphate concentration and a value corresponding to the determined pH of the system directly to one of a computer or controller means; and d) one of a computer or controller means for determining the sodium to phosphate ratio of said system based upon the values corresponding to the determined phosphate concentration of the system and the determined pH of the system and for automatically controlling the feed rate of at least one water treatment chemical being added to said system so as to maintain pH, phosphate concentration and sodium to phosphate ratio within desired ranges.

7. The apparatus of claim 6 wherein said FIA means further comprises:

a) filter means and three-way valve means for establishing a filtered, continuously flowing sample stream from said system to waste, from which sample units may be selected at designated intervals;

b) mixing valve means having two switchable modes of operation including that when a sample unit is not to be analyzed and two reagent composition streams comprising a color-forming reagent and a reducing agent are brought together and admixed on a continuous basis and that when a sample unit is to be analyzed and the reducing agent stream is interrupted and the filtered sample stream is substituted therefor for sufficient time to select a sample unit, which then becomes admixed with the color-forming reagent stream while bounded in front and behind by said reducing agent stream when the flow of the reducing agent is restored, thereby forming a reaction mixture of the sample unit, color-forming regent and reducing agent, c) a first conduit means for separately connecting and carrying the sample stream and the two reagent composition streams to said mixing valve means;

d) container means for the two reagent compositions, connected to said mixing valve means by said first conduit means;

e) a second conduit means from said mixing valve means, and eventually to waste, for carrying the reaction mixture stream formed by mixing of the sample stream and the two reagent composition streams during and subsequent to passage through said mixing valve means, said second conduit means being of sufficient length to permit completion of the colorimetric reaction in the reaction mixture stream;

f) heating means through which the second conduit means passes for heating of the reaction mixture stream;

g) a colorimeter through which the second conduit means passes, having a 600–850 nm filter for reading the signal produced by the reaction mixture stream;

h) computer means which process the data from the colorimeter means together with other data which results in calculation of the concentration of total orthophosphate contained in the boiler system from which the sample stream was obtained; and i) means for maintaining a pressure of from 2–10 psig throughout the FIA apparatus, whereby the sample, reagent composition, and reaction mixture streams are individually and collectively impelled through said means to waste.

8. The apparatus of claim 6 wherein said FIA means further comprises:

a) filter means, selector valve means, and injection valve means for establishing a filtered, continuously flowing sample stream from said boiler system to waste, from which sample units may be selected at designated intervals for passage through the FIA apparatus, by switching of the injection valve means;

b) said injection valve means recited above and separate mixing connector means which are connected and operate together so as to have two switchable modes of operation, the first being when a sample unit is not to be analyzed and two reagent composition streams comprising a color-forming reagent and a reducing agent are brought together and admixed on a continuous basis at and by the mixing connector means, the color-forming reagent flowing directly into said mixing connector means, and the reducing agent flowing into said mixing connector means after first passing through said injection valve means, and the second being when a sample unit is to be analyzed and the stream of reducing agent is interrupted by switching of said injection valve means and the filtered sample stream is substituted therefor for sufficient time to select a sample unit, which then becomes admixed at said mixing connector means with the color-forming reagent stream while bounded in front and behind by said reducing agent stream when the flow of the reducing agent is restored, thereby forming a reaction mixture of the sample unit, color-forming regent and reducing agent;

c) a first conduit means having two branches for separately connecting and carrying the sample stream and the reducing agent stream to said injection valve means and from there a single branch to said mixing connector means, and a second conduit means for directly connecting and carrying the color-forming reagent stream to said mixing connector means without passing through said injection valve means;

d) container means for the two reagent compositions, connected to said injection valve means and said mixing valve means by said first and second conduit means;

e) a third conduit means from said mixing connector means, and eventually to waste, for carrying the reaction mixture stream formed by mixing of the sample stream and the two reagent composition streams during and subsequent to passage through said mixing connector means, said third conduit means being of sufficient length to permit completion of the colorimetric reaction in the reaction mixture stream;

f) heating means through which the third conduit means passes for heating of the reaction mixture stream;

g) a colorimeter through which the second conduit means passes, having a 600–850 nm filter for reading the signal produced by the reaction mixture stream;

h) computer means which process the data from the colorimeter means together with other data which results in calculation of the concentration of total orthophosphate contained in the boiler system from which the sample stream was obtained; and i) means for maintaining a pressure of from 2–10 psig, throughout the FIA apparatus, whereby the sample, reagent composition, and reaction mixture streams are individually and collectively impelled through said means to waste.

* * * * *

UNITED STATES PATENT AND TRADEMARK OFFICE
CERTIFICATE OF CORRECTION

PATENT NO. : 5,747,342
DATED : May 5, 1998
INVENTOR(S) : John D. Zupanovich

It is certified that error appears in the above-identified patent and that said Letters Patent is hereby corrected as shown below:

Title Page, under [54] title, line 2, after "PH" insert comma.

Column 1 Line 2 in the title after "PH" insert comma.

Title page, [57] ABSTRACT, line 13, after "pH, a" delete "means" and insert --device--.

Column 3 Line 5 "concentration" should read --concentrations--.

Column 3 Line 63 "is done" should read --are done--.

Column 4 Line 14 "disclose" should read --discloses--.

Column 4 Line 21 after "Operating" delete period --.--.

Column 4 Line 56 "disclose" should read --discloses--.

Column 5 Line 31 after "monitor," delete "preferable" and insert --preferably--.

Column 5 Line 34 "preferable a computer" should read --preferably a computer--.

Column 8 Line 61 "continous" should read --continuous--.

Column 9 Line 4 "continously" should read --continuously--.

Column 11 Line 34 "efficiently" should read --efficiency--.

Column 12 Line 3 "mixing, valve" should read --mixing valve--.

Column 16 Line 34 "content" should read --contents--.

UNITED STATES PATENT AND TRADEMARK OFFICE
CERTIFICATE OF CORRECTION

PATENT NO. : 5,747,342
DATED : May 5, 1998
INVENTOR(S) : John D. Zupanovich

It is certified that error appears in the above-identified patent and that said Letters Patent is hereby corrected as shown below:

Column 19 Claim 7 paragraph b) Line 33 "regent" should read --reagent--.

Column 20 Claim 8 paragraph b) Line 28 "regent" should read --reagent--.

Signed and Sealed this

First Day of December, 1998

Attest:

BRUCE LEHMAN

*Attesting Officer*          Commissioner of Patents and Trademarks